(12) United States Patent
Cuppoletti

(10) Patent No.: US 7,205,099 B2
(45) Date of Patent: Apr. 17, 2007

(54) METHODS FOR STUDYING ION CHANNELS INCORPORATED ONTO A SOLID-SUPPORTED MEMBRANE

(76) Inventor: John Cuppoletti, 56 Bayham Dr., Cincinnati, OH (US) 45218

( * ) Notice: Subject to any disclaimer, the term of this patent is extended or adjusted under 35 U.S.C. 154(b) by 410 days.

(21) Appl. No.: 10/448,957

(22) Filed: May 30, 2003

(65) Prior Publication Data

US 2004/0038421 A1 Feb. 26, 2004

Related U.S. Application Data

(60) Provisional application No. 60/385,193, filed on May 31, 2002.

(51) Int. Cl.
*C12Q 1/00* (2006.01)
*G01N 27/26* (2006.01)
*G01N 33/53* (2006.01)

(52) U.S. Cl. .................... 435/4; 435/7.1; 205/777.5; 205/789.5; 205/793.5

(58) Field of Classification Search ............... 436/149; 435/4, 7.1; 205/777.5, 789.5, 793.5
See application file for complete search history.

(56) References Cited

U.S. PATENT DOCUMENTS 5,919,576 A * 7/1999 Hui et al. .................... 428/545
6,541,071 B1 * 4/2003 Bookbinder et al. ..... 427/407.2

OTHER PUBLICATIONS

Cheng et al. 2001.Langmuir, vol. 17, pp. 1240-1242.*

Pintschovirus J., et al, Charge translocation by the Na+/K+ -ATPase investigated on solid supported membranes; cytoplasmic cation binding and release. *Biophys J* 76(2): 827-836, 1999.

Pintschovius J., et al, Translocation by the NA+/K+ -ATPase investigated on solid supported membranes rapid solution exchange with a new technique. *Biophys J* Feb.;(76(2): 814-826, 1999.

Florin E-L and Gaub HE, Painted supported lipid membranes. *Biophysical Journal* 64:375-383, 1993.

Seifert K, et al, Transport by ion translocating membrane proteins on solid supported membranes. *Biophysical Journal* 64:384-391, 1993.

Parak WJ, et al, Electrically excitable normal rat kidney fibroblasts; A new model system for cell-semiconductor hybrids. *Biophys J* 76(3): 1659-6, 1999.

Remjeesingh M., et al, Quarternary structure of the chloride channel CIC-2. *Biochemistry* Nov. 14, 2000; 39(45): 13838-13847.

Sullivan E., et al, Measurement of [$Ca^{2+}$] using the Fluorometric Imaging Plate Reader (FLIPR). *Method Mol Biol* 114: 125-133, 1999.

Tewari KP, et al, PKA and arachidonic acid activation of human recombinant CIC-2 chloride channels. *AM J Physiol Cell Physiol* 279(1):C40-50, 2000.

(Continued)

*Primary Examiner*—Maryam Monshipouri
(74) *Attorney, Agent, or Firm*—Dinsmore & Shohl LLP; Denise M. Everett

(57) ABSTRACT

Methods for studying ion channels comprise incorporating an ion channel onto the surface of a solid-supported membrane; applying a potential to the solid-supported membrane; and measuring an electrical signal of the ion channel. Methods for identifying or screening compounds that bind to ion channels employ an ion channel incorporated onto a solid-supported membrane.

13 Claims, 10 Drawing Sheets

OTHER PUBLICATIONS

Stroffekova K., et al, Identification of the pH sensor and activation by chemical modification of the ClC-2G Cl-channel. *Am J Physiol* 275 (4 Pt 1): C1113-23, 2000.

Sherry AM, et al, Characterization of the human pH- and PKA-activated ClC-2G(2 alpha) Cl- channel. *AM J Physiol* 273 (2 Pt 1): C384-93, 1997.

* cited by examiner ium layer, a gold layer, a lipid mercaptan monolayer, a lipid monolayer, and membrane fragments. Specifically, the silanized glass support 20 is layered with a chromium layer 22, and then a gold layer 24, which is reacted with a lipid mercaptan monolayer 26. This lipid mercaptan monolayer is then coated with a lipid monolayer 28, to form a lipid-bilayer. Membrane fragments 30 are then absorbed. Membrane fragments are prepared by homogenization of cells. The cells containing ion channels may come from any species and contain either wild type or recombinant native, engineered proteins, or synthetic ion channels. The membrane fragments may be derived from membranes that are unpurified or purified by any of a variety of biochemical techniques. Furthermore, the membranes may be either closed (vesicles), detergent solutions, micelles, or broken sheets of cells. Organic and fluorocarbon solutions of ion channels may also be used.

METHODS FOR STUDYING ION CHANNELS INCORPORATED ONTO A SOLID-SUPPORTED MEMBRANE

RELATED APPLICATION

This application claims priority under 35 U.S.C. §119(e) of U.S. Provisional Application Ser. No. 60/385,193 filed May 31, 2002.

FIELD OF THE INVENTION

The present invention is directed toward methods for studying ion channels. The methods comprise incorporating an ion channel onto a solid-supported membrane; applying a potential to the solid-supported membrane; and measuring an electrical signal of the ion channel. Additionally, the invention is directed toward methods for identifying or screening compounds that bind to ion channels incorporated onto a solid-supported membrane.

BACKGROUND OF THE INVENTION

Conventional methods for studying ion channels have relied on indirect measurement approaches, which require the use of intact cells and methods that are often not easily interpretable or are not sufficiently sensitive and/or accurate. Furthermore, the planar lipid-bilayers and the patch clamp approach that are conventionally utilized lack stability and size, which prevent the membrane from being reacted with multiple substances, washed and even re-used for multiple cycles.

SUMMARY OF INVENTION

Accordingly, it is an object of the invention to provide novel methods for studying ion channels. It is a further object to provide methods for studying ion channels, which methods employ using solid-supported membranes.

It is yet a further object of the invention to provide methods for identifying or screening compounds that bind to ion channels incorporated onto solid-supported membranes.

In accordance with one aspect of the invention, there are provided methods for studying ion channels. The methods comprise incorporating an ion channel onto a solid-supported membrane; applying a potential to the solid-supported membrane; and measuring an electrical signal of the ion channel.

In accordance with another aspect of the invention, there are provided methods for identifying or screening compounds that bind to ion channels. The methods comprise contacting a ion channel incorporated onto a solid-supported membrane with a compound to be identified or screened; applying a potential to the solid-supported membrane; and measuring an electrical signal of the ion channel.

The present methods are advantageous for facilitating the study of ion channels and compounds that bind to the ion channel. Additional embodiments, objects and advantages of the invention will become more fully apparent in view of the following detailed description.

DETAILED DESCRIPTION OF THE DRAWINGS

DETAILED DESCRIPTION

The present inventor has found that solid-supported membranes can be used for the purpose of studying the electrical properties of ion transport proteins and ion channels, and further, for the study of rapid electrical events associated with these transport proteins. Methods in accordance with the present invention incorporate an ion channel onto a solid-supported membrane to study not only the ion channel, but also, compounds that bind to the ion channel.

More specifically, the methods for studying ion channels comprise incorporating an ion channel onto a solid-supported membrane; applying a potential to the solid-supported membrane; and measuring an electrical signal of the ion channel. Furthermore, methods for identifying or screening compounds that bind to an ion channel comprise contacting an ion channel incorporated onto a solid-supported membrane with a compound to be identified or screened; applying a potential to the solid-supported membrane; and measuring an electrical signal of the ion channel.

Figure 1:
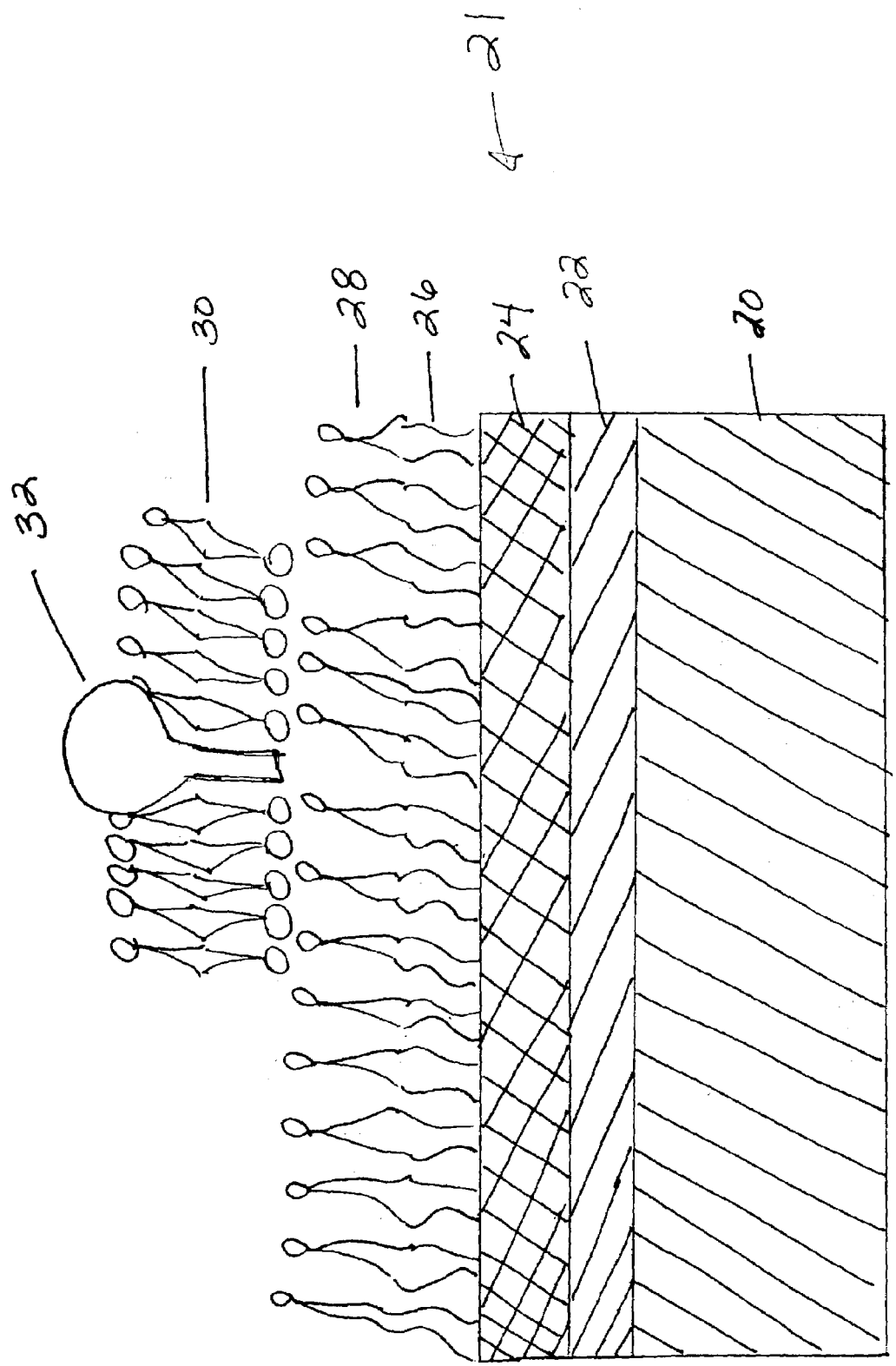
FIG. 1 illustrates a schematic view of a solid-supported membrane suitable for use in the methods of the invention.

FIG. 1 illustrates a solid-supported membrane 21, which may be used in the present invention. The membrane of FIG. 1 comprises a silanized glass support 20, a chrom One skilled in the art will appreciate that the layers of the solid-supported membrane may comprise various thicknesses. Furthermore, as the underlying structures of the solid-supported membrane do not contribute to the processes leading to insertion of the ion channel into the membrane, porous supports may be used to support the lipid bilayers with ion channels. Other supports that may be suitable include, but are not limited to, agar polymers, conducting polymers, glass, alkylated hydrogels, alumina membranes, bilayers supported by surface layer proteins from prokaryotes and archeabacteria, or combinations thereof.

Moreover, one skilled in the art will recognize the various methods suitable for incorporating an ion channel onto a solid-supported membrane. The ion channels may be incorporated by adding the ion channels in aqueous solutions of de-ionized water or in physiological salt solutions. While not wishing to be bound by theory, the inventor believes that solution treatments that increase the binding and fusion of membrane proteins and vesicles with lipid bilayers or cells may be effective in increasing fusion with the lipid bilayers on the surface of the gold slides. In fact, the incorporation of ion channels can be aided by the addition of divalent cations or by the addition of polyethylene glycol or other fusogenic agents. While not wishing to be bound by theory, the inventor also believes that the addition of viral fusion proteins and other agents may also increase the rate of binding and incorporation of ion transport proteins. Alternatively, treatments may be used to attach proteins directly or indirectly to surfaces of solid supported membranes. For example, the proteins may be modified to contain an SH group on an appropriately sized spacer arm, or may be attached covalently or non-covalently to bifunctional groups that react with both the protein of the ion channel and the solid support. Further, these methods may be fully or partially automated by robotics.

In one embodiment of the invention, the ion channel is incorporated onto the surface of the solid-supported membrane. In a further embodiment of the invention, the ion channel is incorporated onto a lipid-bilayer of the solid-supported membrane. As illustrated in FIG. 1, an ion channel is incorporated onto the surface of the membrane, for example, in a well 32. A suitable well enables a connection of the electrode with the bathing solution on the surface of the the ion channel-containing membrane. Arrays or a single well may be formed using various techniques known in the art, including, but not limited to, etching, mechanical treatment, heating of the insulated area to achieve contact with the underlying substratum, or by the formation of a random set of holes in an insulating surface covering the face of the solid-supported membrane using a grid design for application of the insulating layer, and forming defects within the insulating area. Suitable defects may be formed by mechanical treatment in the insulating layer or heating. After formation of the various layers, the defects may be probed with a small electrode until a defect with suitable electrical properties is identified. All other defects within the well are then closed by application of an insulating material. The appropriate electrical properties for the defect area depends upon the membranes used, the ion channels to be studied, and the properties of the drugs to be screened.

After the ion channel is incorporated onto the solid-supported membrane, a potential is applied to the solid-supported membrane. In accordance with one embodiment of the present invention, potential is applied by connecting an external electrode of a digitizer-amplifier to the solid-supported membrane, although other techniques may be employed. For example, the gold layer 24 may be connected to an external electrode of a digitizer-amplifier. In a further embodiment of the invention, the applied potential may be varied and direct electrical measurements can then be made on this system. One skilled in the art will appreciate the variation of the applied potential. For example, the potential may be varied from −80 to +80 mV.

Figure 2:
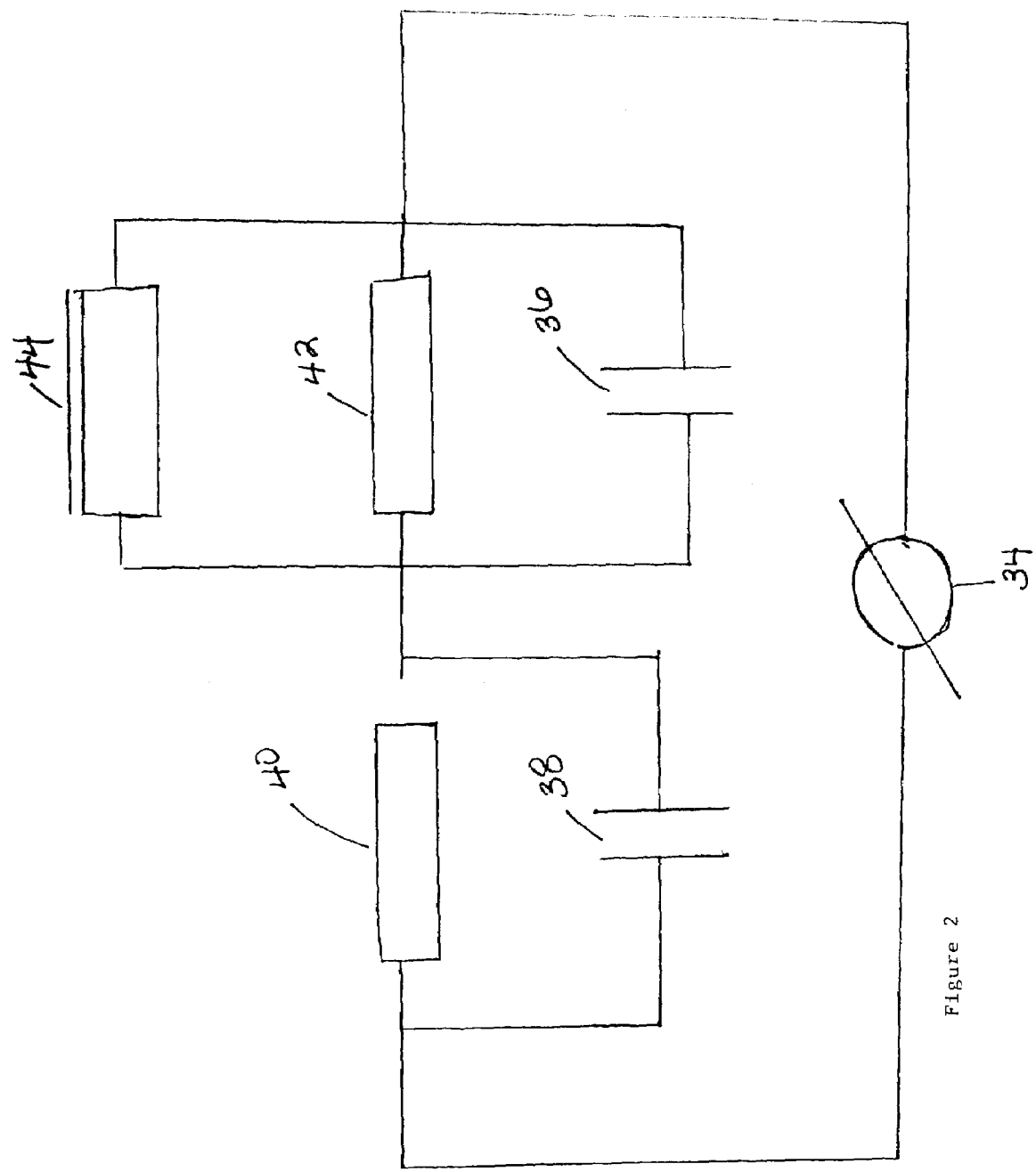
FIG. 2 illustrates an equivalent circuit of a membrane system suitable for use in the methods of the invention.

As illustrated in FIG. 2, the electrical signal generated by the ion channels derived from the solid-supported membrane 21 is characterized by the specific capacitances, Cp 36 and Cm 38, and the specific conductances, Gp 42 and Gm 40 of the membrane fragments 30 and the solid-supported membrane 21, respectively. The electrical circuit that generates the electrical signals includes Ip(t) 44, the time-dependent channel current passed by the ion channel, and I(t) 34, the time dependent current which is measured in the outer circuit.

In a further embodiment of the invention, the potential is applied after the ion channel is contacted with the compound to be identified or screened. One skilled in the art will appreciate the various methods for contacting an ion channel incorporated onto a solid-supported membrane with a compound to be identified or screened. The methods include, but are not limited to, contacting the compound with the ion channel in aqueous solutions of de-ionized water or physiological salt solutions. Further, these methods may be fully or partially automated by robotics.

The synthetic, solid-supported membrane employed in the present invention is significantly more stable than planar lipid bilayers and the patch clamp approach that are conventionally utilized for studies of ion channels. The stability of the present solid-supported membranes as compared to their conventional equivalents is on the order of days. Further, the high mechanical stability of the solid-supported membrane also allows the membrane to be reacted with multiple substances, washed and even re-used for multiple cycles. Due to this stability, the membrane can be larger than even planar lipid bilayers. For example, the solid-supported membrane may be of relatively large size encompassing literally hundreds of square micrometers for a membrane patch as compared to the conventional equivalent, typically encompassing approximately 1 square micrometer.

The large size of the solid-supported membrane allows for incorporation of many copies of the ion channel onto the surface of the solid-supported membrane. These ion channels may produce large currents that may be detected directly by single and inexpensive amplifiers connected with one or more of the wells formed on the surface of the solid-supported membrane. Ion channels have very high transport rates (billions of ions per see) and the density of ion channels can be very high in simple expression/purification systems. Existing amplifiers are therefore easily configured to carry out the measurements of the present invention. A single amplifier and digitizer with commercially available software can handle up to 16 different membranes for current measurements lasting approximately 1 second each. Six parallel digitizer-amplifier systems can handle 96 samples (16×6 samples) in approximately 16 seconds. This rate allows high throughput screening of thousands of samples on each such system.

Furthermore, large libraries of compounds can be rapidly screened by noting whether mixtures of such compounds affect an electrical signal from an ion channel sensor device. If the mixture is without effect, other mixtures may be used. Therefore, it is possible to screen many compounds at once. Once it has been demonstrated that the mixture affects the compound, less complex mixtures may be prepared until the active compound is discovered. Alternatively, single compounds may be screened for an effect on an ion channel sensor that has been prepared in the wells.

Therefore, the present invention has advantages over the prior indirect measurement approaches, which require the use of intact cells and methods that are often not easily interpretable or are not sufficiently sensitive and/or accurate. For example, the FLIPR method attempts to use changes in intracellular calcium to monitor effectors of various ion channels (Sullivan, et al, *Methods Mol Biol* 114: 125–133, 1999). That approach suffers from the possibility that elements of the reporting system, rather than the ion channel itself, may be affected by the tested agent. Furthermore, the present approach has the added advantage that sidedness studies, predicting which side is intracellular and which is extracellular, may be undertaken.

The use of solid-supported membranes containing ion channels have immense importance as sensors for rapid screening of pharmacologically active compounds in the biomedical fields, for quality control of foods and beverages (including olfaction and taster receptors) and for environmental and smart sensors. Furthermore, the wide availability of literally hundreds of cloned ion channels and useful mutants, coupled with simple expression and purification systems, makes the present invention useful with many different systems.

EXAMPLE

Figure 3A:
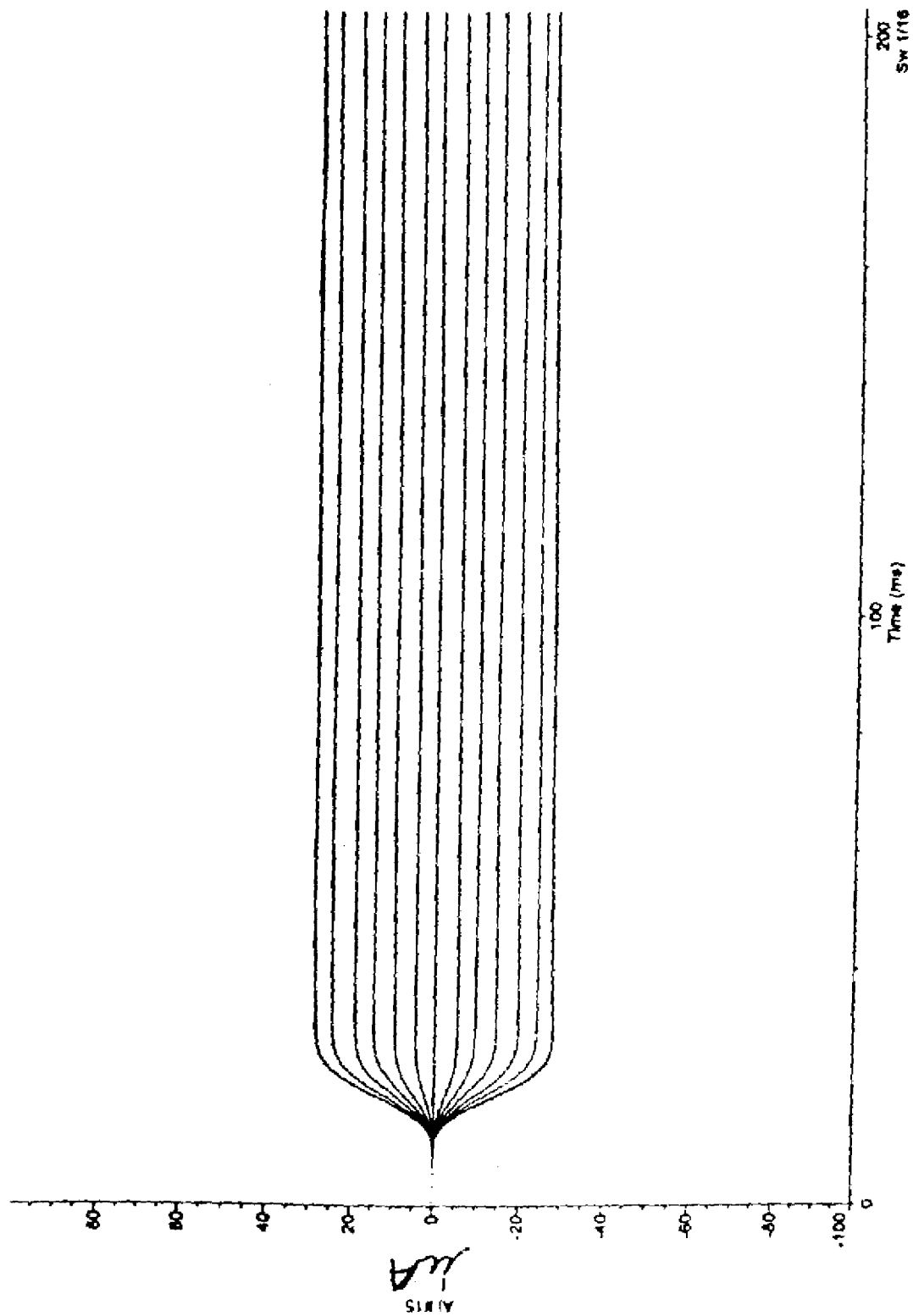
FIG. 3A shows the currents measured using pClamp 5.5 software 20 minutes after addition of a membrane, according to the invention as described in the Example.
Figure 3B:
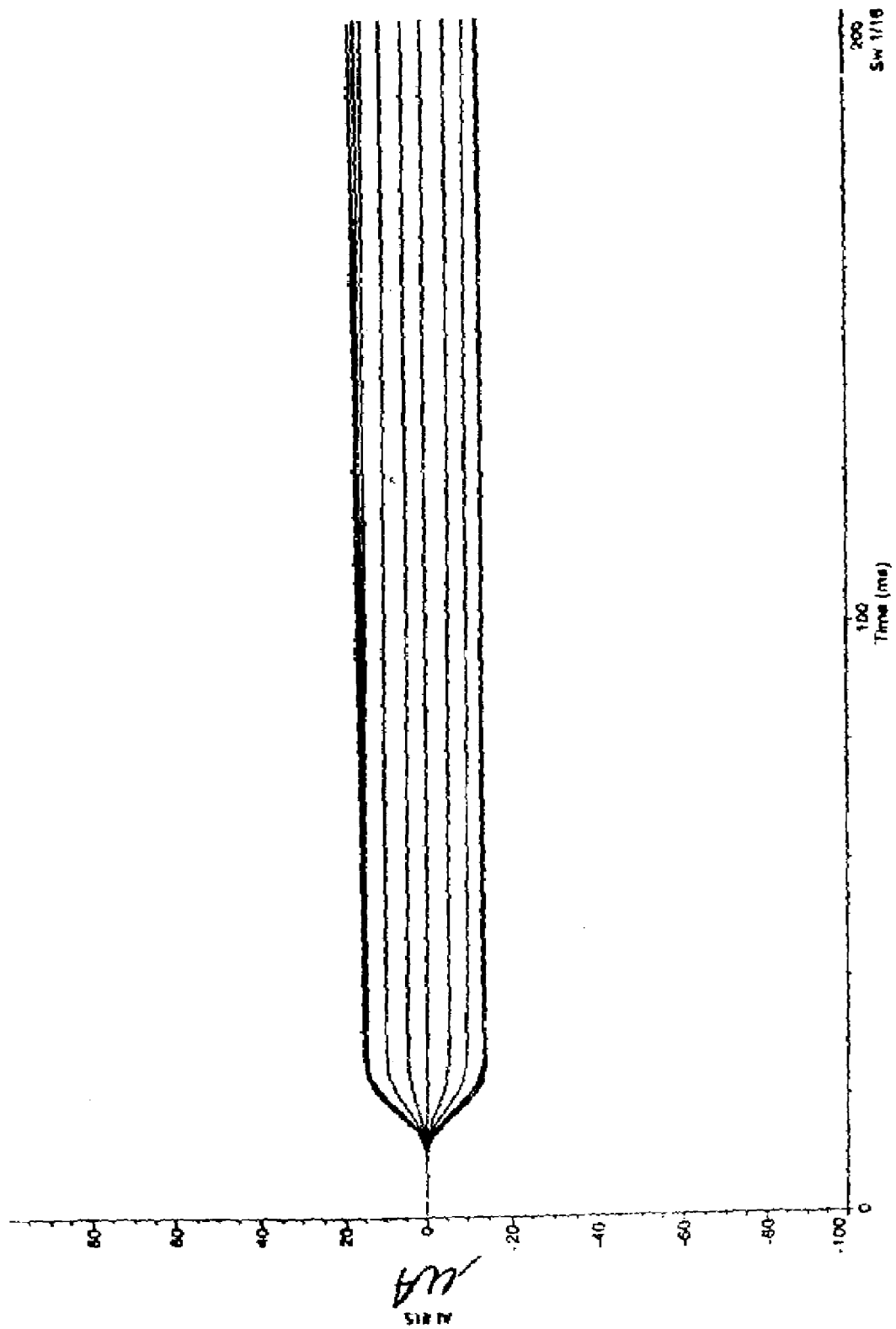
FIG. 3B shows the currents after incubation with increasing concentrations of PG490798, an inhibitor of Kv1.5 channels, with the final concentration of drug being 100 nM.
Figure 3C:
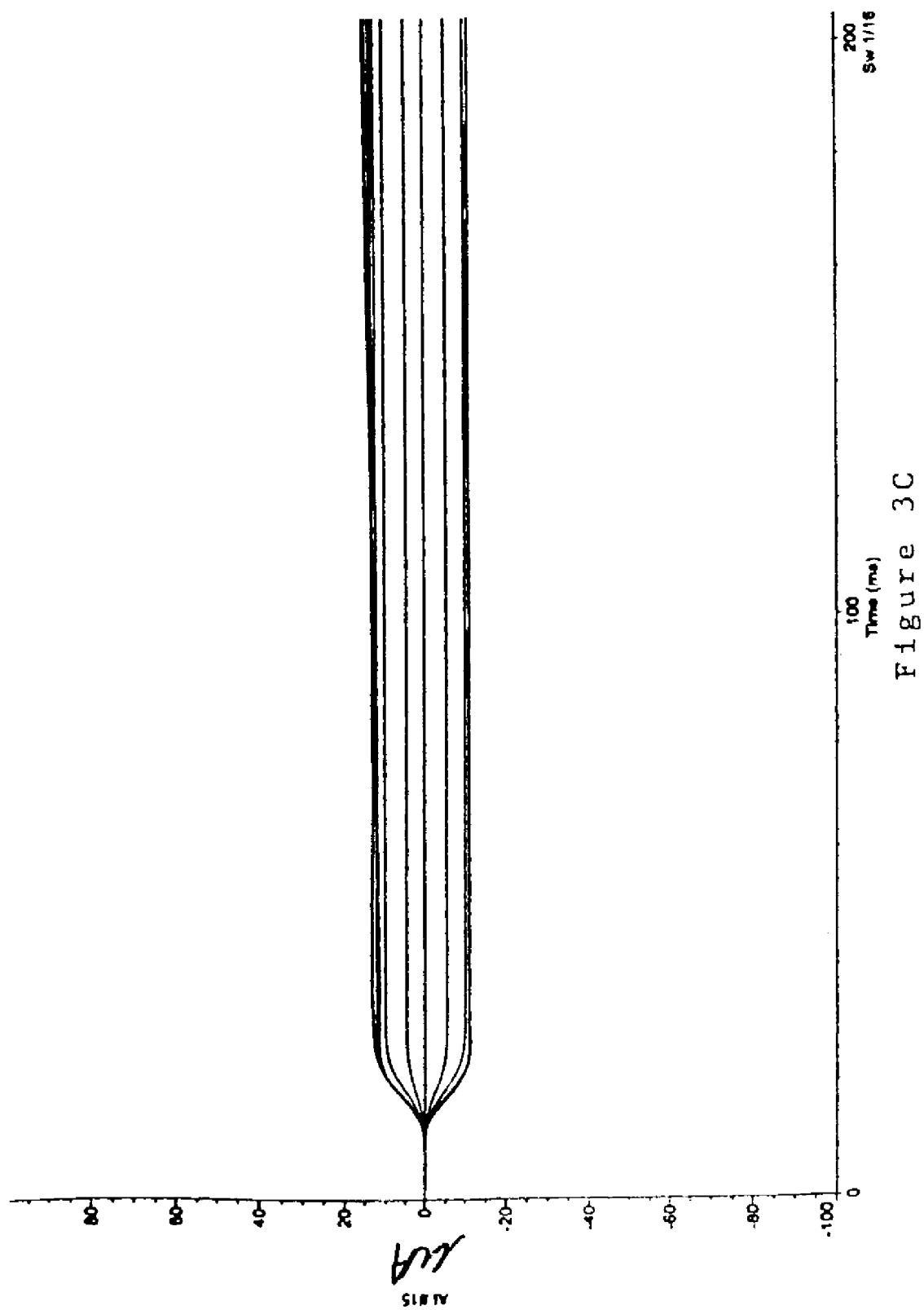
FIG. 3C shows the currents after incubation with increasing concentrations of PG490798, with final concentration of drug being 190.5 nM.
Figure 3D:
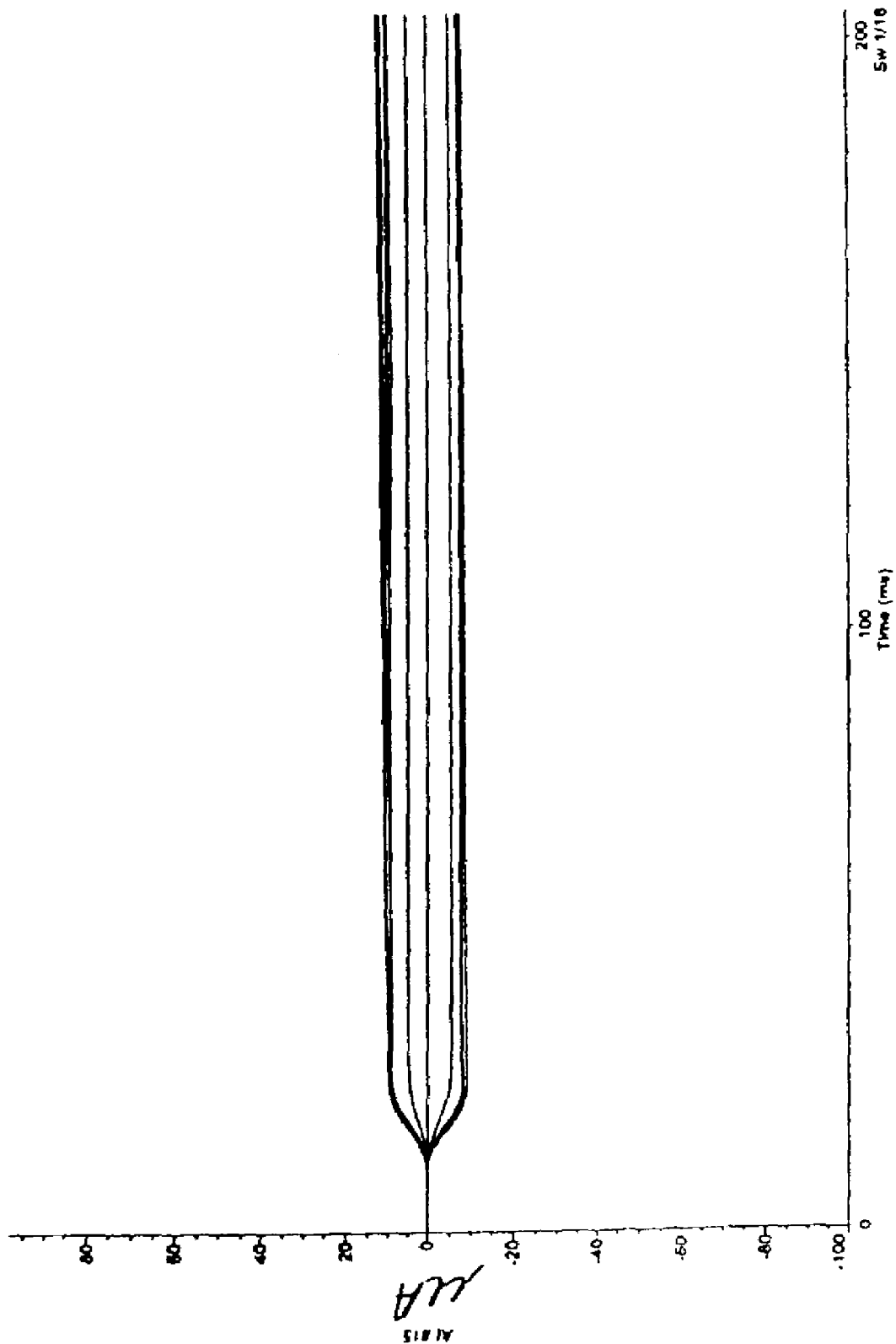
FIG. 3D shows the currents after incubation with increasing concentrations of PG490798, with the final concentration of drug being 347.8 nM.
Figure 3E:
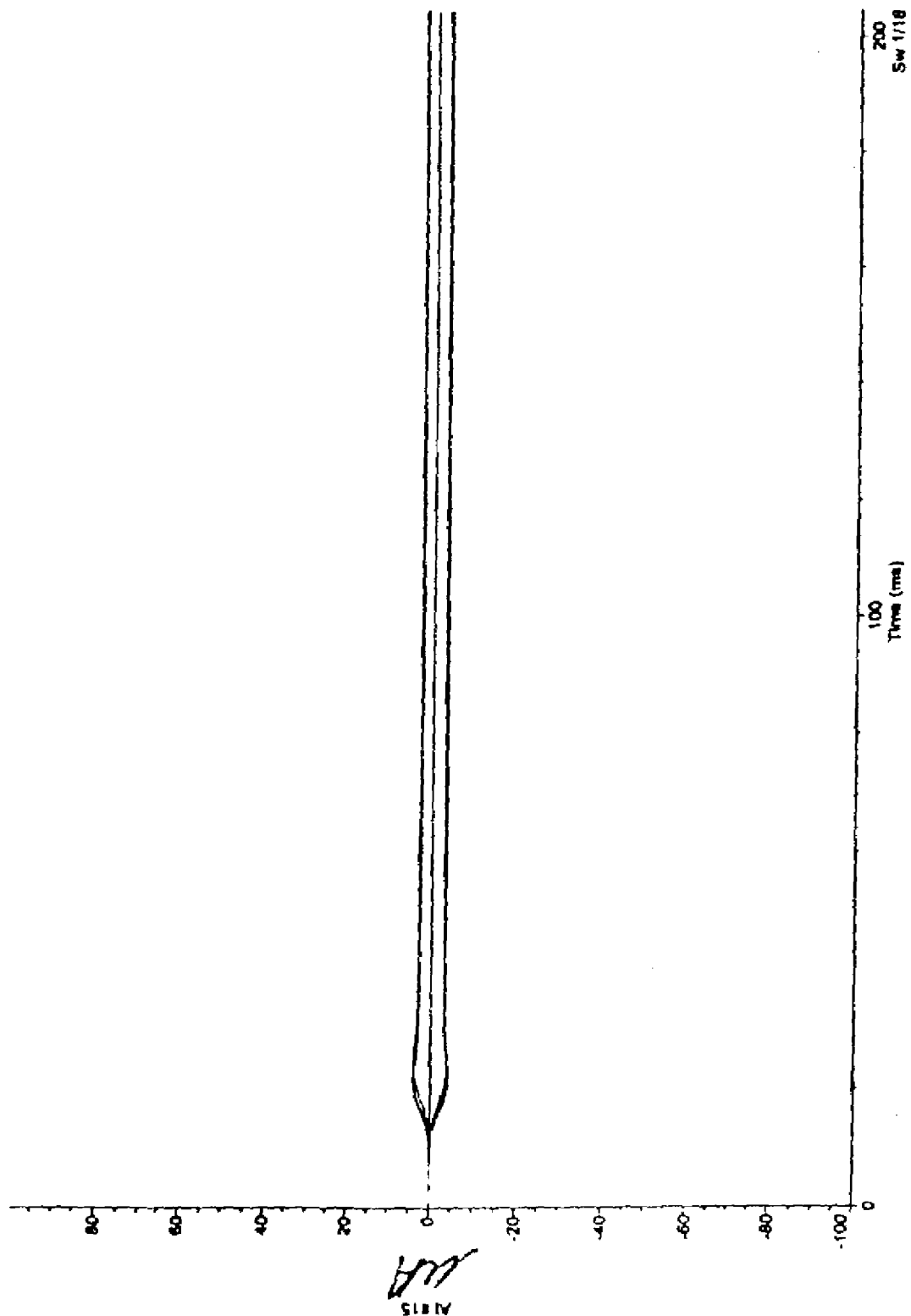
FIG. 3E shows the currents after incubation with increasing concentrations of PG490798, with the final concentration of drug being 592.5 nM.
Figure 3F:
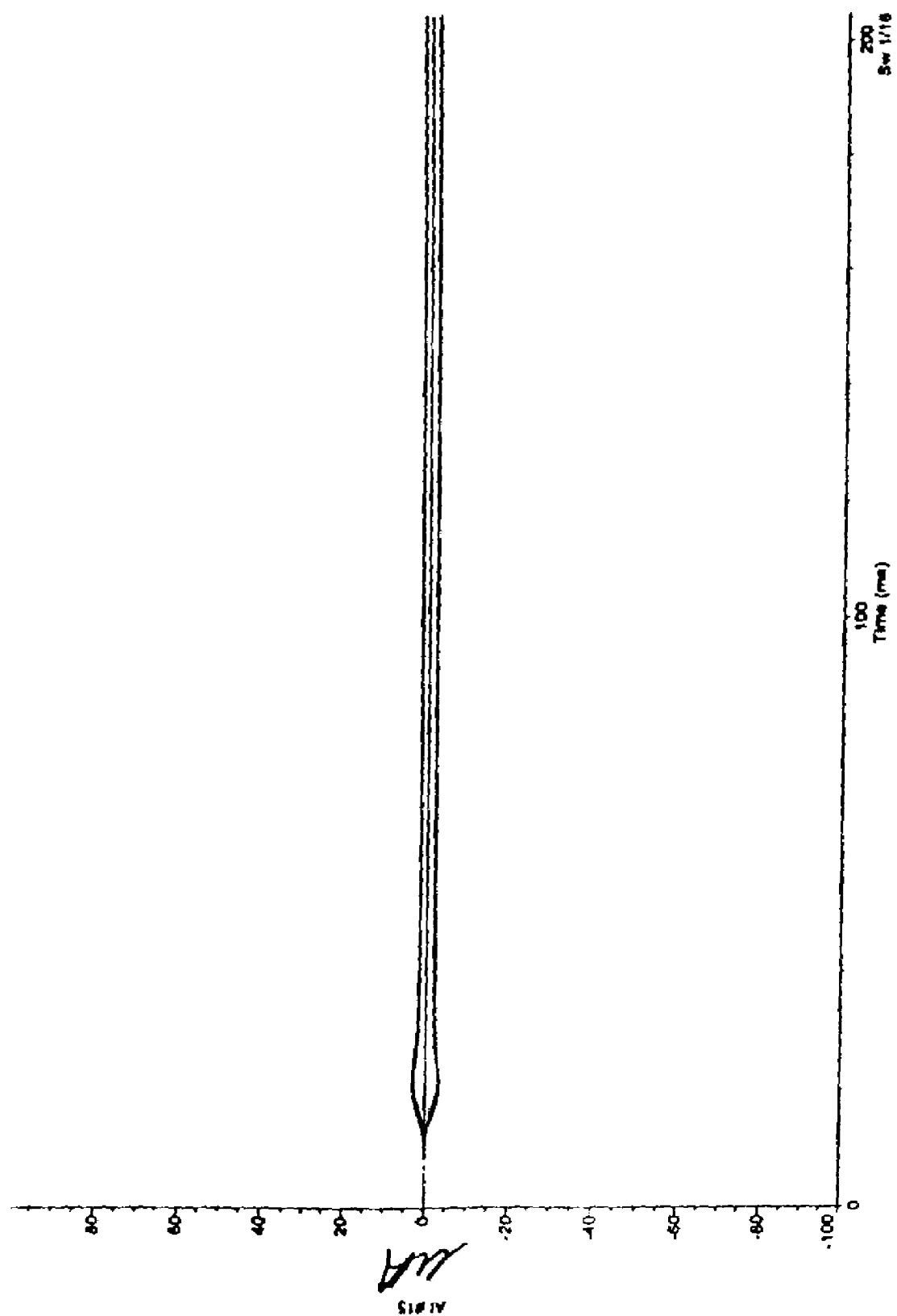
FIG. 3F shows the currents after incubation with increasing concentrations of PG490798, with the final concentration of drug being 770.4 nM.

This example demonstrates the response of Kv1.5 channel protein to PG490798, an inhibitor of Kv1.5 channels, using a method according to the present invention and a solid-supported membrane, as described in FIG. 1. Isolated wells on the gold and lipid coated layer of the solid-supported membrane are formed using Devcon 5 minute epoxy (Product 14250). The wells are constructed by the formation of a random set of holes in an insulating surface covering the face of the solid supported membrane using a grid design for application of the insulating layer, and forming defects within the insulating area. These spontaneous or engineered holes form wells with the appropriate properties for channel insertion and pharmacological studies of the channel. A suspension of membranes from cells expressing recombinant Kv1.5 channel protein are added to the prepared well on the membrane. Currents are measured using pClamp 5.5 software 20 minutes after addition of the membranes, as depicted in FIG. 3A. Voltage pulses from −80 to +80 mV are applied for 200 mS, and resultant currents are recorded. Currents are recorded after incubation with increasing concentrations of PG490798. The final concentration of drug in the respective trials is 100 nM, 190.5 nM, 347.8 nM, 592.5 nM, and 770.4 nM, depicted in FIGS. 3B–F, respectively. Incubations are for 2 minutes before each recording session is commenced. The solution used for all recordings contains 130 mM potassium methylsulfonate, 1 mM ethylene glucol-bis(beta-aminoethyl ether)-N,N,N',N'-tetraacetic acid, and 10 mM (N-(2-hydroxyethyl)piperazine-N'-(2ethanesulfonic acid)), adjusted to pH 7.4 with KOH.

Figure 4:
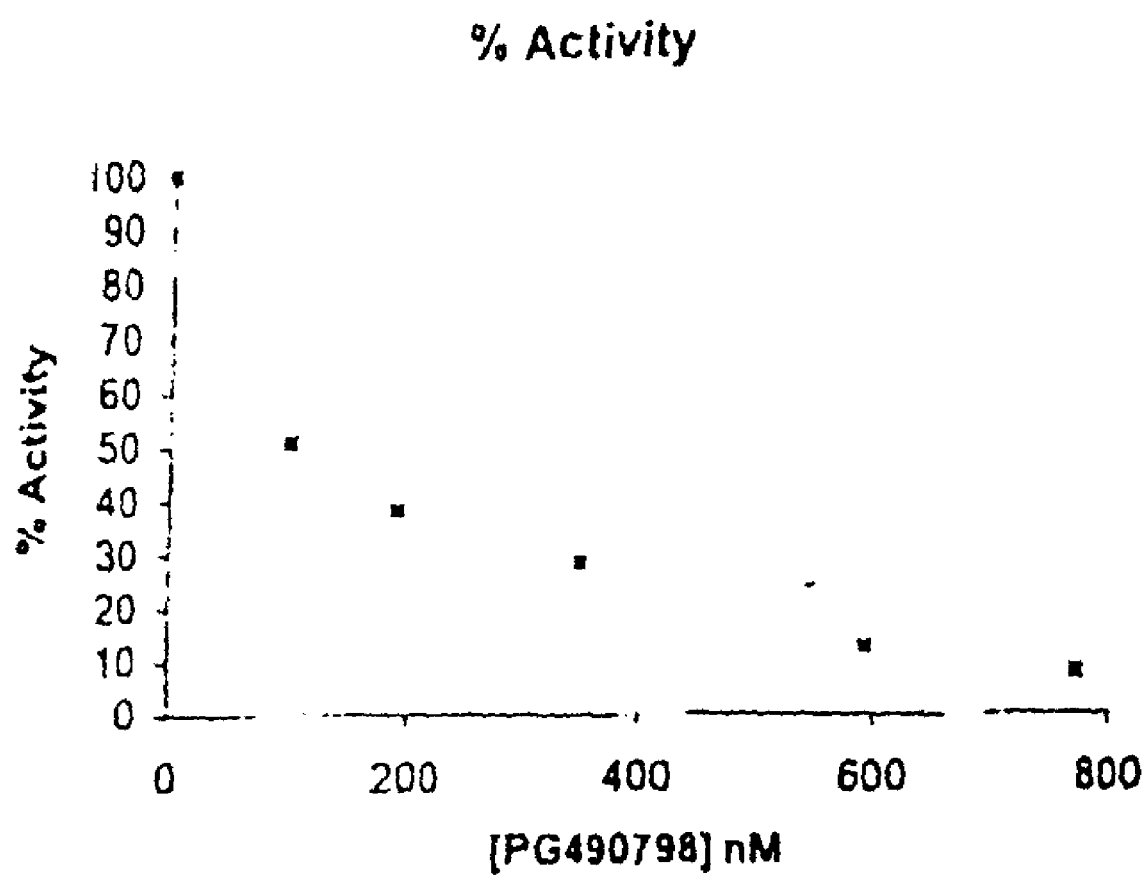
FIG. 4 shows a dose dependent decrease in channel currents, plotted as a function of the concentration of PG490798, derived from fractional currents at −80 mV for each of the recordings of FIGS. 3A–F.

To analyze the data, a dose response curve for response of Kv1.5 channels to PG49078 is obtained. Fractional currents at −80 mV are determined for each of the recordings and plotted as a function of the concentration of PG490798, showing a dose dependent decrease in channel currents, as depicted in FIG. 4. Further analysis is performed by obtaining the currents (in microamps), as measured by averaging the currents from 40 msec to 100 msec using pClamp clampfit 8.0 software, as depicted in Table 1.

TABLE 1

|  | A1d18c52 | A1d18c52 | A1d18c55 | A1d18c55 | A1d18c58 | A1d18c58 | A1d18c61 |
|---|---|---|---|---|---|---|---|
| 1 | −80 | −28.1627 | −80 | −14.3825 | −80 | −10.8657 | −80 |
| 2 | −70 | −27.7696 | −70 | −14.0774 | −70 | −11.0074 | −70 |
| 3 | −60 | −27.5855 | −60 | −14.2212 | −60 | −11.1622 | −60 |
| 4 | −50 | −24.3638 | −50 | −13.9036 | −50 | −11.3571 | −50 |
| 5 | −40 | −19.8236 | −40 | −13.9723 | −40 | −11.4504 | −40 |
| 6 | −30 | −14.6853 | −30 | −13.5461 | −30 | −11.3373 | −30 |
| 7 | −20 | −10.0048 | −20 | 10.1064 | −20 | −10.1527 | −20 |
| 8 | −10 | −5.46263 | −10 | −5.51514 | −10 | −5.51774 | −10 |
| 9 | 0 | −0.053564 | 0 | −0.0555827 | 0 | −0.0571305 | 0 |
| 10 | 10 | 4.5451 | 10 | 4.59424 | 10 | 4.63867 | 10 |
| 11 | 20 | 9.81421 | 20 | 9.91203 | 20 | 9.96094 | 20 |
| 12 | 30 | 14.5996 | 30 | 14.706 | 30 | 12.998 | 30 |
| 13 | 40 | 19.2407 | 40 | 16.0637 | 40 | 12.037 | 40 |
| 14 | 50 | 24.6585 | 50 | 14.9839 | 50 | 11.7157 | 50 |
| 15 | 60 | 28.8308 | 60 | 15.5809 | 60 | 12.1483 | 60 |
| 16 | 70 | 28.8345 | 70 | 15.2487 | 70 | 12.1532 | 70 |

|  |  | A1d18c61 | A1d18c65 | A1d18c65 | A1d18c68 | A1d18c68 |
|---|---|---|---|---|---|---|
|  | 1 | −8.08759 | −80 | −3.56421 | −80 | −2.27629 |
|  | 2 | −8.06856 | −70 | −3.47677 | −70 | −2.20109 |
|  | 3 | −8.99327 | −60 | −3.3912 | −60 | −2.13143 |
|  | 4 | −7.80531 | −50 | −3.31366 | −50 | −2.05981 |
|  | 5 | −8.05435 | −40 | −3.23766 | −40 | −2 |
|  | 6 | −7.8236 | −30 | −3.1658 | −30 | −1.948 |
|  | 7 | −8.20263 | −20 | −3.12176 | −20 | −1.89331 |
|  | 8 | −5.56959 | −10 | −3.06019 | −10 | −1.8374 |
|  | 9 | −0.0600145 | 0 | −0.0630223 | 0 | −0.0784505 |
|  | 10 | 4.68725 | 10 | 2.96838 | 10 | 1.63232 |
|  | 11 | 9.31384 | 20 | 2.9202 | 20 | 1.60018 |
|  | 12 | 10.5015 | 30 | 2.85886 | 30 | 1.57796 |
|  | 13 | 9.0666 | 40 | 2.77582 | 40 | 1.54858 |

TABLE 1-continued

| 14 | 9.44506 | 50 | 2.72107 | 50 | 1.53092 |
| 15 | 10.6893 | 60 | 2.6192 | 60 | 1.51318 |
| 16 | 10.4496 | 70 | 2.54482 | 70 | 1.49471 |

Figure 5:
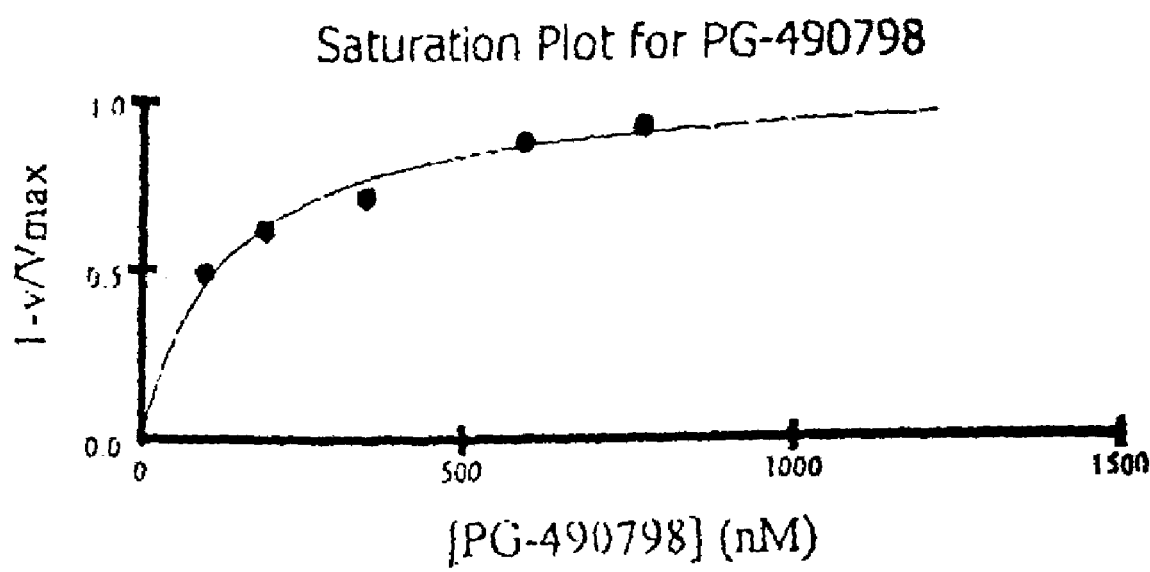
FIG. 5 shows fractional inhibition (1-v/Vm) plotted as a function of dose using commercial software, to obtain the half maximal inhibition constant 129 nM.

Finally, currents at −80 mV at the indicated concentrations of PG490798 are normalized by dividing by the currents at −80 mV in the absence of PG490798 (v/Vm). This fractional inhibition (1-v/Vm) is then plotted as a function of dose using commercial software (EZ-fit, Perrella Scientific), to obtain the half maximal inhibition constant 129 nM, as depicted in FIG. 5 using the Michaelis-Menten Enzyme Kinetic Model wherein Km is 1.29E+02+/−2.39E+01, Vmax is 1.05E+00+/−5.42E−02, Runs Test is Pass p=0.05, and Goodness-of-Fit Criterion is −1.181.

The specific embodiments and example described herein are illustrative in nature only and are not intended to be limiting of the claimed methods. Additional embodiments and variations within the scope of the claimed invention will be apparent to those of ordinary skill in the art in view of the present disclosure.

What is claimed:

1. A method of studying potassium ion channels, comprising the steps of:
    (a) incorporating membrane fragments comprising the potassium ion channel protein onto a solid-supported lipid membrane;
    (b) applying a potential to the solid-supported membrane; and
    (c) measuring an electrical signal of the ion channel protein,
    wherein the solid-supported membrane comprises a support, a lipid bilayer, and membrane fragments, and, further wherein the lipid bilayer is a lipid mercaptan monolayer and a lipid monolayer.

2. The method according to claim 1, wherein the solid-supported membrane further comprises a chromium layer and a gold layer.

3. The method according to claim 2, wherein the chromium layer is formed on the support.

4. The method according to claim 3, wherein the gold layer is formed on the chromium layer.

5. The method according to claim 4, wherein the gold layer is reacted with the lipid mercaptan monolayer.

6. The method according to claim 5, wherein the lipid mercaptan monolayer is coated with the lipid monolayer.

7. The method according to claim 6, wherein the membrane fragments are absorbed into the lipid monolayer.

8. The method according to claim 1, wherein the support of the solid-supported membrane comprises agar polymers, conducting polymers, glass, alkylated hydrogels, alumina membranes, bilayers supported by surface layer proteins from prokaryotes or archeabacteria, or combinations thereof.

9. The method according to claim 1, wherein the support is a porous support.

10. The method according to claim 1, wherein the ion channel protein is incorporated onto the surface of the solid-supported membrane.

11. The method according to claim 10, wherein the ion channel protein is incorporated onto a lipid bilayer of the solid-supported membrane.

12. The method according to claim 1, wherein the applied potential is varied.

13. The method according to claim 1, further comprising a step of connecting an external electrode of a digitizer-amplifier to the solid-supported membrane.

* * * * *